(12) United States Patent
Shisa et al.

(10) Patent No.: US 9,273,328 B2
(45) Date of Patent: Mar. 1, 2016

(54) YEAST MUTANT OF KLUYVEROMYCES AND METHOD FOR ETHANOL PRODUCTION USING THE SAME

(75) Inventors: Noriko Shisa, Nisshin (JP); Rinji Akada, Ube (JP); Hisashi Hoshida, Ube (JP); Takeshi Uemura, Yokohama (JP); Kozue Mutaguchi, Yokohama (JP); Kenro Tokuhiro, Aichi-gun (JP); Satoshi Katahira, Nagoya (JP)

(73) Assignee: TOYOTA JIDOSHA KABUSHIKI KAISHA, Aichi (JP)

( * ) Notice: Subject to any disclaimer, the term of this patent is extended or adjusted under 35 U.S.C. 154(b) by 0 days.

(21) Appl. No.: 14/008,446

(22) PCT Filed: Mar. 26, 2012

(86) PCT No.: PCT/JP2012/057704
§ 371 (c)(1),
(2), (4) Date: Sep. 27, 2013

(87) PCT Pub. No.: WO2012/133275
PCT Pub. Date: Oct. 4, 2012

(65) Prior Publication Data
US 2014/0024097 A1 Jan. 23, 2014

(30) Foreign Application Priority Data
Mar. 30, 2011 (JP) ................... 2011-076715

(51) Int. Cl.
| | | |
|---|---|---|
| C12P 7/06 | (2006.01) | |
| C12N 15/81 | (2006.01) | |
| C12N 9/04 | (2006.01) | |
| C12P 7/10 | (2006.01) | |

(52) U.S. Cl.
CPC ............. *C12P 7/06* (2013.01); *C12N 9/0006* (2013.01); *C12N 15/815* (2013.01); *C12P 7/10* (2013.01); *Y02E 50/16* (2013.01); *Y02E 50/17* (2013.01)

(58) Field of Classification Search
None
See application file for complete search history.

(56) References Cited

FOREIGN PATENT DOCUMENTS

| JP | 2005-514951 A | 5/2013 |
|---|---|---|
| WO | 03/062430 A1 | 7/2003 |

OTHER PUBLICATIONS

Accession X60224. Apr. 18, 2005.*
Ladriere et al. Biochim Biophys Acta. Apr. 29, 1993;1173(1):99-101.*
Chica et al. Curr Opin Biotechnol. Aug. 2005;16(4):378-84.*
Sen et al. Appl Biochem Biotechnol. Dec. 2007;143(3):212-23.*
Accession Q07288. Feb. 1, 1995.*
Accession B2R487. Jul. 1, 2008.*
Ladriere J.M. et al., Sequence of a gene coding for a cytoplasmic alcohol dehydrogenase, Alcohol dehydrogenase, Feb. 8, 2011, p. 3,5 & 6.
Lertwattanasakul, N., et al., Comparison of the Gene Expression Patterns of Alcohol Dehydrogenase Isozymes in the Thermotolerant Yeast Kluyveromyces marxianus and Their Physiological Functions, alcohol dehydrogenase IV, Jun. 14, 2007, p. 4 & 5.
Vladimir Leskovac, et al., "The three zinc-containing alcohol dehydrogenases from bakers yeast, *Saccharomyces cerevisiae*", FEMS Yeast Research, 2002, pp. 481-494.
Olga De Smidt, et al., "The alcohol dehydrogenases of *Saccharomyces cerevisiae*: a comprehensive review", Department of Microbial, 2008, pp. 967-978.
Hermann J. Heipieper, et al., "Ethanol tolerance and membrane fatty acid adaptation in adh multiple and null mutants of Kluyveromyces lactis", Department of Biology, Third University of Rome, May 24, 2000, pp. 777-784.
Noppon Lertwattanasakul, et al., "Comparison of the Gene Expression Patterns of Alcohol Dehydrogenase Isozymes in the Thermotolerant Yeast Kluyveromyces marxianus and Their Physiological Functions", Department of Biological Chemistry, Yamaguchi University, May 7, 2007, pp. 1170-1182.
Ladriere J.M. et al., Sequence of a gene coding for a cytoplasmic alcohol dehydrogenase, from Kluyveromyces marxianus ATCC 12424, Alcohol dehydrogenase, Feb. 8, 2011, three pages total.
Lertwattanasakul, N., et al., Comparison of the Gene Expression Patterns of Alcohol Dehydrogenase Isozymes in the Thermotolerant Yeast Kluyveromyces marxianus and Their Physiological Functions, alcohol dehydrogenase IV, Jun. 14, 2007, two pages total.

* cited by examiner

*Primary Examiner* — Christian Fronda
(74) *Attorney, Agent, or Firm* — Sughrue Mion, PLLC

(57) ABSTRACT

A yeast of the genus *Kluyveromyces* is modified to improve the ethanol yield from xylose by attenuation of at least one gene selected from the group consisting of the ADH1 gene derived from *Kluyveromyces marxianus*, a gene functionally equivalent to the ADH1 gene, the ADH4 gene derived from *Kluyveromyces marxianus*, and a gene functionally equivalent to the ADH4 gene.

3 Claims, 15 Drawing Sheets

Fig. 7

```
ScADH1:KmADH1 (79/97---Identity/Similarity)
Query Sequence
  File Name       :
  Sequence Name   : ScADH1p.prj
  Sequence Size   : 349

Target Sequence
  File Name       : KmADH1pMAIP1047.prj
  Sequence Name   : KmADH1pMAIP1047.prj
  Sequence Size   : 348

Unit Size to Compare = 2
  Pick up Location No. = 1

Query Range: 1 - 348
Sbjct Range: 1 - 348
348 bp, INT.Score: 1445, OPT.Score: 1452
Identity: 277 / 348 (79%)
Similarity: 339 / 348 (97%)

Query   1    MSIPETQKGVIFYESHGKLEYKDIPVPKPKANELLINVKYSGVCHTDLHAWHGDWPLPVK   60
             |.|| |||||||||. |.|.|| |||||||.|||| |||||||| |||| ||.|||| .|
Sbjct   1    MAIPETQKGVIFYENGGELQYKDIPVPKPKPNELLINVKYSGVCHTDLHAWQGDWPLDTK   60

Query   61   LPLVGGHEGAGVVVGMGENVKGWKIGDYAGIKWLNGSCMACEYCELGNESNCPHADLSGY  120
             |||| ||||||.||.|| ||.| .|||||| |||||||| ||.|| ||.| |||.||||
Sbjct   61   LPLVGGHEGAGIVVAMGENVTGWEIGDYAGIKWLNGSCMSCEECELSNEPNCPKADLSGY  120

Query   121  THDGSFQQYATADAVQAAHIPQGTDLAQVAPILCAGITVYKALKSANLMAGHWVAISGAA  180
             |||| |||||||||||||| .|...|||.|| |||| .|||||| |...||.|||||||
Sbjct   121  THDGSFQQYATADAVQAARIPKNVDLAEVAPILCAGVTVYKALKSAIIKAGDWVAISGAC  180

Query   181  GGLGSLAVQYAKAMGYRVLGIDGGEGKEELFRSIGGEVFIDFTKEKDIVGAVLKATDGGA  240
             |||| ||.||||||||||||||.|...|..|  ...|  |||||| .||. ...|..|||
Sbjct   181  GGLGSLAIQYAKAMGYRVLGIDAGDEKAKLFKELGGEYFIDFTKTKDMVAEVIEATNGGA  240

Query   241  HGVINVSVSEAAIEASTRYVRANGTTVLVGMPAGAKCCSDVFNQVVKSISIVGSYVGNRA  300
             |.|| ||||||||..|. |.|. ||.||||.| .|. |||||||||||||||||||||||
Sbjct   241  HAVINVSVSEAAISTSVLYTRSNGTVVLVGLPRDAQCKSDVFNQVVKSISIVGSYVGNRA  300

Query   301  DTREALDFFARGLVKSPIKVVGLSTLPEIYEKMEKGQIVGRYVVDTSK    348
             |||| ||||.||||.| |..| |....|.||.| ||.|| |||  ||||
Sbjct   301  DTREALDFFSRGLVKAPIKILGLSELATVYDKMSKGQIIGRIVVDTSK    348
```

Fig. 8

```
ScADH1:KmADH2 (86/96)
[ GENETYX : Homology Data ]
Date : 2010.10.23
Query Sequence
    File Name        :
    Sequence Name    : ScADH1p.prj
    Sequence Size    : 349

Target Sequence
    File Name        : KmADH2pMSIP1047.prj
    Sequence Name    : KmADH2pMSIP1047.prj
    Sequence Size    : 348

Unit Size to Compare = 2
    Pick up Location No. = 1

Query Range: 1 - 348
Sbjct Range: 1 - 348
348 bp, INT.Score: 1512, OPT.Score: 1512
Identity: 300 / 348 (86%)
Similarity: 336 / 348 (96%)

Query   1    MSIPETQKGVIFYESHGKLEYKDIPVPKPKANELLINVKYSGVCHTDLHAWHGDWPLPVK   60
             |||.||||||||.|.|  ||||||.|||||  ||||||||||||.||    .|
Sbjct   1    MSIPTTQKGVIFYENGGQLYYKDIPVPKPKSNELLINVKYSGVCHTDLHAWKGDWPLDTK   60

Query   61   LPLVGGHEGAGVVVGMGENVKGWKTGDYAGIKWLNGSCMACEYCELGNESNCPHADLSGY  120
             |||   |||||||||.||.||  |||| ||||||||||| .|| |||.||||||.  |||
Sbjct   61   LPLVGGHEGAGVVVAMGDNVKGWKIGDLAGIKWLNGSCMNCEECELSNESNCPDADLSGY  120

Query   121  THDGSFQQYATADAVQAAHIPQGTDLAQVAPILCAGITVYKALKSANLMAGHWVAISGAA  180
             |||  ||||||||||||.   ||||||||||.  ||||....||.||   |||
Sbjct   121  THDGSFQQYATADAVQAAHIPAGTDLAQVAPILCAGVTVYKALKTAAMKAGDWVAISGAA  180

Query   181  GGLGSLAVQYAKAMGYRVLGIDGGEGKEELFRSIGGEVFIDFTKEKDIVGAVLKATDGGA  240
             |||  ||||||||.|||  ||||||.|.|||    ||||.||||.|.|   .|||
Sbjct   181  GGLGSLAVQYAKAMGFRVLGIDGGEGKEELFKSLGGEVFIDFTKSKDIVGEVIKATNGGA  240

Query   241  HGVINVSVSEAAIEASTRYVRANGTTVLVGMPAGAKCCSDVFNQVVKSISIVGSYVGNRA  300
             |||  ||||  |||.|.|  . ||.||||.|.|||   ||||||||||  ||||||||||
Sbjct   241  HGVINVSVSEKAIESSIEYCRSNGTVVLVGLPKDAKCKSDVFNQVVKSIHIVGSYVGNRA  300

Query   301  DTREALDFFARGLVKSPIKVVGLSTLPEIYEKMEKGQIVGRYVVDTSK 348
             |||   |||  |||| ||||||||||||||.|.  ||||||||
Sbjct   301  DTREALDFFCRGLVHAPIKVVGLSTLPEIYEKMEQGKILGRYVVDTSK 348
```

Fig. 9

ScADH1:KmADH3 (79/96)
Query Sequence
  File Name      :
  Sequence Name : ScADH1p.prj
  Sequence Size : 349

Target Sequence
  File Name      : KmADH3pMLRL1128.prj
  Sequence Name : KmADH3MLRL1128+-_1
  Sequence Size : 375

Unit Size to Compare = 2
  Pick up Location No. = 1

Query Range: 1 - 348
Sbjct Range: 28 - 375
348 bp, INT.Score: 1427, OPT.Score: 1435
Identity: 275 / 348 (79%)
Similarity: 336 / 348 (96%)

```
Query    1   MSIPETQKGVIFYESHGKLEYKDIPVPKPKANELLINVKYSGVCHTDLHAWHGDWPLPVK   60
             ..||.|||  |||. ||||||  |||||.||.|||  ||||||||||||||.  ||..|
Sbjct   28   VAIPEKQKGVIFYENGGKLEYKDIPVPKPKPNEILINVKYSGVCHTDLHAWKGDWPLATK   87

Query   61   LPLVGGHEGAGVVVGMGENVKGWKIGDYAGIKWLNGSCMACEYCELGNESNCPHADLSGY  120
             ||||||||||||| ||.||||||. ||||||||||||||.||.||.||||||.|||||
Sbjct   88   LPLVGGHEGAGVVVAMGENVKGWEIGDYAGIKWLNGSCMSCEFCELSNESNCPDADLSGY  147

Query  121   THDGSFQQYATADAVQAAHTPQGTDLAQVAPILCAGITVYKALKSANLMAGHWVAISGAA  180
             |||||||||| ||||||.||. |  ||..|||||||. |||||.|.|.||. |  |||||
Sbjct  148   THDGSFQQYATADAVQAARTPKGTDLAETAPILCAGVTVYKALKTAGLKAGDWVAISGAA  207

Query  181   GGLGSLAVQYAKAMGYRVLGTDGGEGKEELFRSIGGEVFIDFTKEKDIVGAVLKATDGGA  240
             |||||||||||||||||. |||||| |||.|.. . .|.|.|.|||.||..|.. .|||.
Sbjct  208   GGLGSLAVQYAKAMGYRVVGTDGGEEKGKLAKQLGAEAFVDFTKTKDMIGEIQEITNGGP  267

Query  241   HGVINVSVSEAATEASTRYVRANGTTVLVGMPAGAKCCSDVFNQVVKSTSTVGSYVGNRA  300
             ||||||||||| ..||.||..| .||||.|||.   |.||..|||||.|.| ||||||
Sbjct  268   HGVINVSVSEAAMNASTQYVRPTGTVVLVGLPAGAVIKSEVFSHVVKSIAIKGSYVGNRA  327

Query  301   DTREALDFFARGLVKSPIKVVGLSTLPEIYEKMEKGQIVGRYVVDTSK  348
             |||||..||   |||||||||||.|.||..|| ||.|. ||||||.|
Sbjct  328   DTREAIEFFAAGKVKSPIKVVGLSELPKVYELMEQGKILGRYVVDTEK  375
```

Fig. 10

```
ScADH1:KmADH4 (80/94)
Query Sequence
    File Name       :
    Sequence Name   : ScADH1p.prj
    Sequence Size   : 349

Target Sequence
    File Name       : KmADH4pMFRL1140.prj
    Sequence Name   : KmADH4pMFRL1140.prj
    Sequence Size   : 379

Unit Size to Compare = 2
    Pick up Location No. = 1

Query Range: 2 - 348
Sbjct Range: 33 - 379
347 bp, INT.Score: 1414, OPT.Score: 1415
Identity: 278 / 347 (80%)
Similarity: 329 / 347 (94%)

Query    2   SIPETQKGVIFYESHGKLEYKDIPVPKPKANELLINVKYSGVCHTDLHAWHGDWPLPVKL   61
             .  ||||||| ||||||| ||||||.||.||||          ||||||.||||||||||
Sbjct   33   AIPESQKGVIFYENGGKLEYKDLPVPKPKPNEILINVKYSGVCHTDLHAWKGDWPLPVKL   92

Query   62   PLVGGHEGAGVVVGMGENVKGWKIGDYAGIKWLNGSCMACEYCELGNESNCPHADLSGYT   121
             |||||||||||||..||||....|||||||||||||||.   | |||| .|||||||||
Sbjct   93   PLVGGHEGAGVVVAKGENVTNFEIGDYAGIKWLNGSCMSCELCEQGYESNCLQADLSGYT   152

Query  122   HDGSFQQYATADAVQAAHIPQGTDLAQVAPILCAGITVYKALKSANLMAGHWVAISGAAG   181
             ||||||||||||||.||.|||||..|||||||.||||||||||.|.|.|.|.||||||||
Sbjct  153   HDGSFQQYATADAVQAAQIPKGTDLAEIAPILCAGVTVYKALKTADLQPGQWIAISGAAG   212

Query  182   GLGSLAVQYAKAMGYRVLGIDGGEGKEELFRSIGGEVFIDFTKEKDIVGAVLKATDGGAH   241
             |||||||||||||| |||||||| |||||||.|.|||||  ||.|... ||.||.| |.|
Sbjct  213   GLGSLAVQYAKAMGLRVLGIDGGPGKEELFKSLGGEVFIDFTKSKDMVADIQEATNGGPH   272

Query  242   GVINVSVSEAAIEASTRYVRANGTTVLVGMPAGAKCCSDVFNQVVKSISIVGSYVGNRAD   301
             ||||||.  || |||..|..|||||.||  |  |.  ..||||||||||.|||||||||
Sbjct  273   GVINVSVSEAAISMSTEYVRPTGVVVLVGLPAHAYVKSEVFSHVVKSISIKGSYVGNRAD   332

Query  302   TREALDFFARGLVKSPIKVVGLSTLPEIYEKMEKGQIVGRYVVDTSK   348
             .||.|||||.|||||||||||||.||..||  || |.|.     |||
Sbjct  333   TREAIDFFTRGLVKSPIKVVGLSELPKVYELMEAGKILGRYVVDTSK   379
```

Fig. 11

ScADH2:KmADH1 (79/97)
Query Sequence
  File Name      :
  Sequence Name  : ScADH2p.prj
  Sequence Size  : 349

Target Sequence
  File Name      : KmADH1pMAIP1047.prj
  Sequence Name  : KmADH1pMAIP1047.prj
  Sequence Size  : 348

Unit Size to Compare = 2
  Pick up Location No. = 1

Query Range: 1 - 348
Sbjct Range: 1 - 348
348 bp, INT.Score: 1442, OPT.Score: 1449
Identity: 277 / 348 (79%)
Similarity: 338 / 348 (97%)

```
Query   1    MSIPETQKAIIFYESNGKLEHKDIPVPKPKPNELLINVKYSGVCHTDLHAWHGDWPLPTK   60
             |.|| |||..|||..|.|...||| |||| |||| |||| |||||| ||||.|||| ||
Sbjct   1    MAIPETQKGVIFYENGGELQYKDIPVPKPKPNELLINVKYSGVCHTDLHAWQGDWPLDTK   60

Query   61   LPLVGGHEGAGVVVGMGENVKGWKIGDYAGIKWLNGSCMACEYCELGNESNCPHADLSGY  120
             |||| |||| |.||.|||| .||. |||| |||||||||| |||.|| ||.|.| |.||
Sbjct   61   LPLVGGHEGAGTVVAMGENVTGWEIGDYAGIKWLNGSCMSCEECELSNEPNCPKADLSGY  120

Query   121  THDGSFQEYATADAVQAAHIPQGTDLAEVAPILCAGITVYKALKSANLRAGHWAAISGAA  180
             |||| ||.| |||||||||.  |.. |||| |||| |.|| |||||...||.|.|| ||
Sbjct   121  THDGSFQQYATADAVQAARIPKNVDLAEVAPILCAGVTVYKALKSAHIKAGDWVAISGAC  180

Query   181  GGLGSLAVQYAKAMGYRVLGIDGGPGKEELFTSLGGEVFIDFTKEKDIVSAVVKATNGGA  240
             |||| ||.| |||| |||| |||| .|. |..|..| ||| |||.| |....||| |||
Sbjct   181  GGLGSLAIQYAKAMGYRVLGIDAGDEKAKLFKELGGEYFIDFTKTKDMVAEVIEATNGGA  240

Query   241  HGIINVSVSEAAIEASTRYCRANGTVVLVGLPAGAKCSSDVFNHVVKSISIVGSYVGNRA  300
             |...|||| |||.|.|.|||..|.||||.|||.|||||.||||.||||||||||| |||
Sbjct   241  HAVINVSVSEAATSTSVLYTRSNGTVVLVGLPRDAQCKSDVFNQVVKSISIVGSYVGNRA  300

Query   301  DTREALDFFARGLVKSPIKVVGLSSLPEIYEKMEKGQIAGRYVVDTSK   348
             ||||.||||.||||.||..|||.... ||. ||| ||||.|||||||
Sbjct   301  DTREALDFFSRGLVKAPIKILGLSELATVYDKMSKGQIIGRIVVDTSK  348
```

Fig. 12

ScADH2:KmADH2 (84/96)
[ GENETYX : Homology Data ]
Date : 2010.10.23
Query Sequence
  File Name        :
  Sequence Name    : ScADH2p.prj
  Sequence Size    : 349

Target Sequence
  File Name        : KmADH2pMSIP1047.prj
  Sequence Name    : KmADH2pMSIP1047.prj
  Sequence Size    : 348

Unit Size to Compare = 2
  Pick up Location No. = 1

Query Range: 1 - 348
Sbjct Range: 1 - 348
348 bp, INT.Score: 1510, OPT.Score: 1510
Identity: 295 / 348 (84%)
Similarity: 337 / 348 (96%)

```
Query    1    MSIPETQKAIIFYESNGKLEHKDIPVPKPKPNELLINVKYSGVCHTDLHAWHGDWPLPTK    60
              |||.|||..||||..|.|.||||.|||.|||||.||||||||||.|||||.|||||.|
Sbjct    1    MSIPTTQKGVIFYENGGQLYYKDIPVPKPKSNELLINVKYSGVCHTDLHAWKGDWPLDTK    60

Query   61    LPLVGGHEGAGVVVGMGENVKGWKIGDYAGIKWLNGSCMACEYCELGNESNCPHADLSGY   120
              |||.||||||||||.|.|||||||||.||||||||||||.||.|.||||.||||||||
Sbjct   61    LPLVGGHEGAGVVVAMGDNVKGWKIGDLAGIKWLNGSCMNCEECELSNESNCPDADLSGY   120

Query  121    THDGSFQEYATADAVQAAHIPQGTDLAEVAPILCAGITVYKALKSANLRAGHWAAISGAA   180
              |||.||.|||||||||||.|||.||||||||.||.||||||||||||..||.|.||||
Sbjct  121    THDGSFQQYATADAVQAAHIPAGTDLAQVAPILCAGVTVYKALKTAAMKAGDWVAISGAA   180

Query  181    GGLGSLAVQYAKAMGYRVLGIDGGPGKEELFTSLGGEVFIDFTKEKDIVSAVVKATNGGA   240
              |||.|||||||||||.||||||||.||||||||.||||||||||||||.||.|..|.|||||
Sbjct  181    GGLGSLAVQYAKAMGFRVLGIDGGEGKEELFKSLGGEVFIDFTKSKDIVGEVIKATNGGA   240

Query  241    HGIINVSVSEAAIEASTRYCRANGTVVLVGLPAGAKCSSDVFNIIVVKSISIVGSYVGNRA   300
              ||.|||||||||.|||.|||.|||||||||||.||.|||||.|||.|||||||||||||
Sbjct  241    HGVINVSVSEKAIESSIEYCRSNGTVVLVGLPKDAKCKSDVFNQVVKSIHIVGSYVGNRA   300

Query  301    DTREALDFFARGLVKSPIKVVGLSSLPEIYEKMEKGQIAGRYVVDTSK    348
              |||.||||.|||..|||||||||.|||||||.|.|||||||||||
Sbjct  301    DTREALDFFCRGLVHAPIKVVGLSTLPEIYEKMEQGKILGRYVVDTSK    348
```

Fig. 13

```
ScADH2:KmADH3 (78/96)
Query Sequence
  File Name        :
  Sequence Name    : ScADH2p.prj
  Sequence Size    : 349

Target Sequence
  File Name        : KmADH3pMLRL1128.prj
  Sequence Name    : KmADH3MLRL1128+-_1
  Sequence Size    : 375

Unit Size to Compare = 2
  Pick up Location No. = 1

Query Range: 1 - 348
Sbjct Range: 28 - 375
348 bp, INT.Score: 1418, OPT.Score: 1426
Identity:   274 / 348 (78%)
Similarity: 335 / 348 (96%)

Query    1   MSIPETQKAIIFYESNGKLEHKDIPVPKPKPNELLINVKYSGVCHTDLHAWHGDWPLPTK   60
             ..|||.||..||||.. |||.||| |||||||| |.| ||| |||||| ||| .|| |.||
Sbjct   28   VAIPEKQKGVIFYENGGKLEYKDIPVPKPKPNEILINVKYSGVCHTDLHAWKGDWPLATK   87

Query   61   LPLVGGHEGAGVVVGMGENVKGWKIGDYAGIKWLNGSCMACEYCELGNESNCPHADLSGY  120
             |||| |||||||||.| ||| ||. |||||| ||| |||.||.||| ||. |||||
Sbjct   88   LPLVGGHEGAGVVVAMGENVKGWEIGDYAGIKWLNGSCMSCEFCELSNESNCPDADLSGY  147

Query  121   THDGSFQEYATADAVQAAHIPQGTDLAEVAPILCAGITVYKALKSANLRAGHWAAISGAA  180
             | ||| |.||||||||| .| .|| |||.|| ||| .|| ||||.|.|.| .|. |||||
Sbjct  148   THDGSFQQYATADAVQAARIPKGTDLAEIAPILCAGVTVYKALKTAGLKAGDWVAISGAA  207

Query  181   GGLGSLAVQYAKAMGYRVLGIDGGPGKEELFTSLGGEVFIDFTKEKDIVSAVVKATNGGA  240
             | |||| ||||||||||||.| |||.|...|. ||.|.|.|||| .|. |||||.
Sbjct  208   GGLGSLAVQYAKAMGYRVVGIDGGEEKGKLAKQLGAEAFVDFTKTKDMIGEIQEITNGGP  267

Query  241   HGIINVSVSEAAIEASTRYCRANGTVVLVGLPAGAKCSSDVFNIIVVKSISIVGSYVGNRA  300
             |.|| ||||||..||.| ...| |||||| |||.|.||.||| ||. || |||||
Sbjct  268   HGVINVSVSEAAMNASTQYVRPTGTVVLVGLPAGAVIKSEVFSHVVKSIAIKGSYVGNRA  327

Query  301   DTREALDFFARGLVKSPIKVVGLSSLPEIYEKMEKGQIAGRYVVDTSK             348
             | |||..||| | ||| |||.||..|| ||. .|  |||||.|
Sbjct  328   DTREAIEFFAAGKVKSPIKVVGLSELPKVYELMEQGKILGRYVVDTEK             375
```

Fig. 14

ScADH2:KmADH4 (80/95)
Query Sequence
  File Name        :
  Sequence Name   : ScADH2p.prj
  Sequence Size   : 349

Target Sequence
  File Name        :
  Sequence Name   : KmADH4pMFRL1140.prj
  Sequence Size   : 379

Unit Size to Compare = 2
  Pick up Location No. = 1

Query Range: 2 - 348
Sbjct Range: 33 - 379
347 bp, INT.Score: 1412, OPT.Score: 1413
Identity: 279 / 347 (80%)
Similarity: 330 / 347 (95%)

```
Query    2   SIPETQKAIIFYESNGKLEHKDIPVPKPKPNELLINVKYSGVCHTDLHAWHGDWPLPTKL   61
             . |.||..||||..||||.||.||||     |.||||||||||||||||.||||   .
Sbjct   33   AIPESQKGVIFYENGGKLEYKDLPVPKPKPNEILINVKYSGVCHTDLHAWKGDWPLPVKL   92

Query   62   PLVGGHEGAGVVVGMGENVKGWKIGDYAGIKWLNGSCMACEYCELGNESNCPHADLSGYT   121
             |  |||||||||||..||||....||||     ||||||||.|| || ||||  .||
Sbjct   93   PLVGGHEGAGVVVAKGENVTNFEIGDYAGIKWLNGSCMSCELCEQGYESNCLQADLSGYT   152

Query  122   HDGSFQEYATADAVQAAHIPQGTDLAEVAPILCAGITVYKALKSANLRAGHWAAISGAAG   181
             |  |||.||||||||||.||.|||||.     ||||.||||||||.|.|...|.| ||
Sbjct  153   HDGSFQQYATADAVQAAQIPKGTDLAEIAPILCAGVTVYKALKTADLQPGQWIAISGAAG   212

Query  182   GLGSLAVQYAKAMGYRVLGIDGGPGKEELFTSLGGEVFIDFTKEKDIVSAVVKATNGGAH   241
             |  |||||||||||| |||||||||||||    .||||||||||.||.|... .||  .
Sbjct  213   GLGSLAVQYAKAMGLRVLGIDGGPGKEELFKSLGGEVFIDFTKSKDMVADIQEATNGGPH   272

Query  242   GIINVSVSEAAIEASTRYCRANGTVVLVGLPAGAKCSSDVFNHVVKSISIVGSYVGNRAD   301
             |. ||||||||. || | ..|.||| ||    |. |.||.|||||||| ||||||||||
Sbjct  273   GVINVSVSEAAISMSTEYVRPTGVVVLVGLPAHAYVKSEVFSHVVKSISIKGSYVGNRAD   332

Query  302   TREALDFFARGLVKSPIKVVGLSSLPEIYEKMEKGQIAGRYVVDTSK   348
             ||||.|||.|||||||||||||.||..   || |.| ||||||||||
Sbjct  333   TREAIDFFTRGLVKSPIKVVGLSELPKVYELMEAGKILGRYVVDTSK   379
```

Fig. 15

```
ScADH1:ScADH2 (93/99---Identity/Similarity)
Query Sequence
  File Name       :
  Sequence Name   : ScADH1p.prj
  Sequence Size   : 349

Target Sequence
  File Name       : ScADH2p.prj
  Sequence Name   : ScADH2p.prj
  Sequence Size   : 349

Unit Size to Compare = 2
  Pick up Location No. = 1

Query Range: 1 - 348
Sbjct Range: 1 - 348
348 bp, INT.Score: 1618, OPT.Score: 1618
Identity: 324 / 348 (93%)
Similarity: 345 / 348 (99%)

Query    1    MSIPETQKGVIFYESHGKLEYKDIPVPKPKANELLINVKYSGVCHTDLHAWHGDWPLPVK    60
              ||||||  |||||| || ||||  || ||||| || |||||||| ||||||||||| |
Sbjct    1    MSIPETQKAIIFYESNGKLEHKDIPVPKPKPNELLINVKYSGVCHTDLHAWHGDWPLPTK    60

Query    61   LPLVGGHEGAGVVVGMGENVKGWKIGDYAGIKWLNGSCMACEYCELGNESNCPHADLSGY   120
              ||||||  || ||||||||| ||||||||| ||||| ||||||||||||| ||||||||
Sbjct    61   LPLVGGHEGAGVVVGMGENVKGWKIGDYAGIKWLNGSCMACEYCELGNESNCPHADLSGY   120

Query    121  THDGSFQQYATADAVQAAHIPQGTDLAQVAPILCAGITVYKALKSANLMAGHWVAISGAA   180
              ||||||  |||||||||||| |||||| | |||||||||||||||||| ||| || |||
Sbjct    121  THDGSFQEYATADAVQAAHIPQGTDLAEVAPILCAGITVYKALKSANLRAGHWAAISGAA   180

Query    181  GGLGSLAVQYAKAMGYRVLGIDGGEGKEELFRSIGGEVFIDFTKEKDIVGAVLKATDGGA   240
              |||||| || |||||||| |||| || |||| || |||||| |||||| |  | |  ||
Sbjct    181  GGLGSLAVQYAKAMGYRVLGIDGGPGKEELFTSLGGEVFIDFTKEKDIVSAVVKATNGGA   240

Query    241  HGVINVSVSEAAIEASTRYVRANGTTVLVGMPAGAKCCSDVFNQVVKSISIVGSYVGNRA   300
              || ||| ||||||||||||  |||| ||||  |||| ||||| | |||||||||||||
Sbjct    241  HGIINVSVSEAAIEASTRYCRANGTVVLVGLPAGAKCSSDVFNHVVKSISIVGSYVGNRA   300

Query    301  DTREALDFFARGLVKSPIKVVGLSTLPEIYEKMEKGQIVGRYVVDTSK    348
              |||||||||||||||||||||| | ||||||||||| |  ||||||||
Sbjct    301  DTREALDFFARGLVKSPIKVVGLSSLPEIYEKMEKGQIAGRYVVDTSK    348
```

YEAST MUTANT OF KLUYVEROMYCES AND METHOD FOR ETHANOL PRODUCTION USING THE SAME

CROSS REFERENCE TO RELATED APPLICATIONS

This application is a National Stage of International Application No. PCT/JP2012/057704 filed Mar. 26, 2013, claiming priority based on Japanese Patent Application No. 2011-076715, filed Mar. 30, 2011, the contents of all of which are incorporated herein by reference in their entirety.

TECHNICAL FIELD

The present invention relates to a mutant yeast of the genus *Kluyveromyces* and a method for ethanol production using the same.

BACKGROUND ART

Lignocellulose-containing biomass is an effective starting material for a useful alcohol, such as ethanol, or an organic acid. Lignocellulose-containing biomass includes woody biomass and herbaceous biomass. Lignocellulose-containing biomass, such as woody biomass, is mainly composed of cellulose, hemicellulose, and lignin. In order to produce a liquid fuel such as ethanol from lignocellulose-containing biomass, cellulose or hemicellulose is hydrolyzed (saccharified) into a constitutive monosaccharide, and the monosaccharide is converted into ethanol via fermentation. Cellulose is composed of glucose, and hemicellulose is mainly composed of arabinose and xylose. When producing ethanol with the use of lignocellulose-containing biomass, accordingly, it is preferable that xylose be effectively used as a fermentation substrate, in addition to glucose.

When producing ethanol from lignocellulose-containing biomass, production costs can be reduced if the saccharification process can be simultaneously carried out with the fermentation process without separating these processes from each other. Such technique is referred to as "the simultaneous saccharification and fermentation process." The simultaneous saccharification and fermentation process requires the use of thermotolerant microorganisms capable of fermentation in the reaction temperature range for a carbohydrase (i.e., about 40 degrees C. or higher) and capable of using the xylose (pentose) as a substrate, in addition to glucose.

Examples of known thermotolerant yeasts include yeasts of the genus *Kluyveromyces*, such as *Kluyveromyces marxianus*. While a yeast of the genus *Kluyveromyces* is capable of ethanol fermentation with the utilization of xylose, the yield thereof has not been sufficient. For example, the results of functional analyses of the alcohol dehydrogenase gene of *Saccharomyces cerevisiae* (including a plurality of isomers) are reported in Non-Patent Documents 1 and 2. Patent Document 1 discloses a recombinant yeast strain capable of isomerizing xylose into xylulose, in which alcohol dehydrogenase activity has been reduced. Based on such finding, however, the influence of the deficiency or destruction of the alcohol dehydrogenase gene on the capacity for ethanol fermentation cannot be determined. In addition, functions of the alcohol dehydrogenase gene of a taxonomically different species (i.e., a yeast of the genus *Kluyveromyces* such as *Kluyveromyces marxianus*) cannot be evaluated.

PRIOR ART DOCUMENTS

Patent Document

Patent Document 1: JP 2005-514951 A

Non-Patent Documents

Non-Patent Document 1: FEMS Yeast Research 2, 2002, pp. 481-494
Non-Patent Document 2: FEMS Yeast Research 8, 2008, pp. 967-978

SUMMARY OF THE INVENTION

Object to be Attained by the Invention

As described above, a yeast of the genus *Kluyveromyces* is capable of assimilating xylose and is thermotolerant, and there are high expectations that such microorganisms will be useful for the simultaneous saccharification and fermentation process. Concerning yeasts of the genus *Kluyveromyces*, however, the ethanol yield from xylose is very poor, and no means for improving such poor yield is known. Under the circumstances as described above, it is an object of the present invention to provide a mutant yeast of the genus *Kluyveromyces* modified so as to improve the ethanol yield from xylose and a method for ethanol production using such mutant yeast.

Means for Attaining the Object

The present inventors have conducted concentrated studies in order to attain the above object. As a result, they discovered that the ethanol yield from xylose of a yeast of the genus *Kluyveromyces* would be remarkably improved by attenuation of a particular gene(s) among a plurality of the alcohol dehydrogenase genes of the yeast, thereby completing the present invention. Specifically, the present invention includes the following features.

(1) A mutant yeast of the genus *Kluyveromyces* obtained by attenuation of at least one gene selected from the group consisting of the ADH1 gene derived from *Kluyveromyces marxianus*, a gene functionally equivalent to the ADH1 gene, the ADH4 gene derived from *Kluyveromyces marxianus*, and a gene functionally equivalent to the ADH4 gene.

(2) The mutant yeast according to (1), wherein the yeast of the genus *Kluyveromyces* is *Kluyveromyces marxianus*.

(3) The mutant yeast according to (1), wherein the gene functionally equivalent to the ADH1 gene is derived from a yeast of the genus *Kluyveromyces* other than *Kluyveromyces marxianus* and encodes any of the proteins (a) to (c) below:

(a) a protein comprising the amino acid sequence as shown in SEQ ID NO: 2;

(b) a protein comprising an amino acid sequence having 90% or higher similarity to the amino acid sequence as shown in SEQ ID NO: 2 and having alcohol dehydrogenase activity; and (c) a protein comprising an amino acid sequence derived from the amino acid sequence as shown in SEQ ID NO: 2 by deletion, substitution, addition, or insertion of 1 or a plurality of amino acids and having alcohol dehydrogenase activity.

(4) The mutant yeast according to (1), wherein the gene functionally equivalent to the ADH4 gene is derived from a yeast of the genus *Kluyveromyces* other than *Kluyveromyces marxianus* and encodes any of the proteins (a) to (c) below:

(a) a protein comprising the amino acid sequence as shown in SEQ ID NO: 4;

(b) a protein comprising an amino acid sequence having 90% or higher similarity to the amino acid sequence as shown in SEQ ID NO: 4 and having alcohol dehydrogenase activity; and (c) a protein comprising an amino acid sequence derived from the amino acid sequence as shown in SEQ ID NO: 4 by deletion, substitution, addition, or insertion of 1 or a plurality of amino acids and having alcohol dehydrogenase activity.

(5) A method for ethanol production comprising: a step of culturing of the mutant yeast according to any of claims 1 to 4 in a xylose-containing medium; and a subsequent step of recovering of ethanol from the medium.

(6) The method for ethanol production according to (5), wherein the step of culturing is carried out in a reaction system containing the mutant yeast, lignocellulose-containing biomass, and a carbohydrase.

This description includes part or all of the content as disclosed in the description and/or drawings of Japanese Patent Application No. 2011-076715, which is a priority document of the present application.

Effects of the Invention

While the ethanol yield from glucose with the use of the mutant yeast according to the present invention is not substantially changed, the ethanol yield from xylose is significantly improved. Accordingly, the mutant yeast according to the present invention is capable of high-yield ethanol production in, for example, a medium containing xylose derived from lignocellulose-containing biomass such as woody biomass.

The method for ethanol production according to the present invention involves the use of a mutant yeast with significantly improved ethanol yield from xylose. Thus, the efficiency of ethanol production can be improved at significant levels.

BRIEF DESCRIPTION OF THE DRAWINGS

FIG. 7 shows the alignment of ADH1 derived from *S. cerevisiae* with ADH1 derived from *K. marxianus*.

FIG. 8 shows the alignment of ADH1 derived from *S. cerevisiae* with ADH2 derived from *K. marxianus*.

FIG. 9 shows the alignment of ADH1 derived from *S. cerevisiae* with ADH3 derived from *K. marxianus*.

FIG. 10 shows the alignment of ADH1 derived from *S. cerevisiae* with ADH4 derived from *K. marxianus*.

FIG. 11 shows the alignment of ADH2 derived from *S. cerevisiae* with ADH1 derived from *K. marxianus*.

FIG. 12 shows the alignment of ADH2 derived from *S. cerevisiae* with ADH2 derived from *K. marxianus*.

FIG. 13 shows the alignment of ADH2 derived from *S. cerevisiae* with ADH3 derived from *K. marxianus*.

FIG. 14 shows the alignment of ADH2 derived from *S. cerevisiae* with ADH4 derived from *K. marxianus*.

FIG. 15 shows the alignment of ADH1 derived from *S. cerevisiae* with ADH2 derived from *S. cerevisiae*.

EMBODIMENTS FOR CARRYING OUT THE INVENTION

Figure 1:
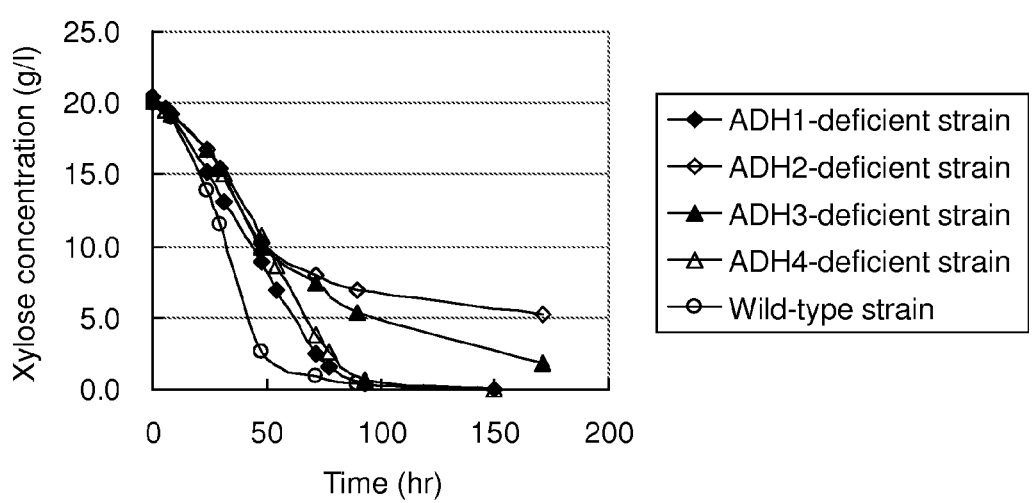
FIG. 1 is a characteristic diagram showing changes in xylose concentration in a xylose-containing medium when four types of ADF-deficient strains are cultured therein.

The mutant yeast according to the present invention is derived from yeast of the genus *Kluyveromyces* by attenuation of a particular alcohol dehydrogenase gene(s), and the ethanol yield thereof from xylose is improved.

Examples of yeasts of the genus *Kluyveromyces* include yeasts such as *K. aestuarii*, *K. africanus*, *K. bacillisporus*, *K. blattae*, *K. dobzhanskii*, *K. hubeiensis*, *K. lactis*, *K. lodderae*, *K. marxianus*, *K. nonfermentans*, *K. piceae*, *K. sinensis*, *K. thermotolerans*, *K. waltii*, *K. wickerhamii*, and *K. yarrowii*. Specifically, the mutant yeast according to the present invention can be prepared by attenuation of a particular alcohol dehydrogenase gene of such yeast of the genus *Kluyveromyces* or a mutant thereof. Use of *Kluyveromyces marxianus*, which is known to be a thermotolerant yeast, as a yeast of the genus *Kluyveromyces* is particularly preferable. *Kluyveromyces marxianus* is not particularly limited. Known strains conserved in a distributable form at depository institutions or mutant strains derived from known strains can be used. An example of a known *Kluyveromyces marxianus* strain is the *Kluyveromyces marxianus* DMKU3-1042 strain. Examples of mutant strains derived from known strains include those derived from the *Kluyveromyces marxianus* DMKU3-1042 strain via destruction of the ura3 or leu2 gene for the purpose of impartation of auxotrophy.

The mutant yeast according to the present invention is obtained by attenuation of a particular alcohol dehydrogenase gene(s). The term "attenuation of gene" refers to reduction of the expression level of such gene and reduction of activity of an enzyme encoded by such gene. The gene expression level can be reduced by, for example, a method comprising destruction or deletion of a particular alcohol dehydrogenase gene, a method comprising destruction or deletion of an expression control region (e.g., a promoter) of such gene, or a method comprising expression of antisense RNA of such gene. Alternatively, the gene expression level can be reduced by, for example, the transposon method, the transgene method, the post-transcriptional gene silencing method, the RNAi method, the nonsense mediated decay (NMD) method, the ribozyme method, the antisense method, the micro-RNA (miRNA) method, or the small interfering RNA (siRNA) method. In addition, an inhibitor of alcohol dehydrogenase may be allowed to react with the gene, so as to reduce activity of an enzyme encoded by such gene. A particular alcohol dehydrogenase gene may be attenuated by performing any such methods in combination.

The mutant yeast according to the present invention has an improved ethanol yield from xylose. In other words, the capacity of the mutant yeast according to the present invention for xylose metabolism is improved. The term "capacity for xylose metabolism" used herein refers to the efficiency for fermentation (i.e., metabolization of xylose contained in a medium) that converts the substance into an alcohol. Thus, an improvement in the capacity for xylose metabolism is synonymous with the improvement in the reaction efficiency of such fermentation. The capacity of a yeast for xylose metabolism can be evaluated by conducting culture in a xylose-containing medium and quantifying the alcohol produced. Also, the capacity of a yeast for xylose metabolism can be evaluated using the uptake rate of xylose contained in a medium (i.e., the consumption rate) as the indicator. The uptake rate of xylose can be determined by serial measurement of the amount of decrease of xylose, the concentration of which at the initiation of culture is known.

The alcohol dehydrogenase gene to be attenuated is a particular alcohol dehydrogenase gene(s) among a plurality of alcohol dehydrogenase genes existing in a yeast of the genus *Kluyveromyces*. Specifically, four types of alcohol dehydrogenase genes of *Kluyveromyces marxianus* (i.e., KmADH1 to KmADH4) are known. The alcohol dehydrogenase genes of *Kluyveromyces marxianus* to be attenuated are the Km ADH1 gene and/or the Km ADH4 gene. The alcohol dehydrogenase genes of yeasts of the genus *Kluyveromyces* other than *Kluyveromyces marxianus* to be attenuated are the ADH gene functionally equivalent to the Km ADH1 gene and/or the ADH gene functionally equivalent to the Km ADH4 gene.

In the yeast of the genus *Kluyveromyces* other than *Kluyveromyces marxianus*, the ADH gene functionally equivalent to the Km ADH1 gene and the ADH gene functionally equivalent to the Km ADH4 gene can be identified by a conventional technique. For example, a plurality of alcohol dehydrogenase genes are first identified in yeasts of the genus *Kluyveromyces* other than *Kluyveromyces marxianus*. From among alcohol dehydrogenases encoded by such genes, subsequently, alcohol dehydrogenase comprising an amino acid sequence exhibiting the highest sequence similarity to the amino acid sequence of the alcohol dehydrogenase encoded by the Km ADH1 gene is identified. The alcohol dehydrogenase gene thus identified can be determined to be a gene functionally equivalent to the Km ADH1 gene of *Kluyveromyces marxianus*. A gene functionally equivalent to the Km ADH4 gene can be identified in the same manner. Sequence similarity is determined using a computer equipped with the BLAST (Basic Local Alignment Search Tool) Program, using the default settings.

The nucleotide sequence of the coding region of the Km ADH1 gene and the amino acid sequence of alcohol dehydrogenase encoded by the Km ADH1 gene are shown in SEQ ID NOs: 1 and 2, respectively. The nucleotide sequence of the coding region of the Km ADH4 gene and the amino acid sequence of alcohol dehydrogenase encoded by the Km ADH4 gene are shown in SEQ ID NOs: 3 and 4, respectively.

The Km ADH1 gene and the Km ADH4 gene existing in *Kluyveromyces marxianus* are not limited to those specifically described above. That is, the Km ADH1 gene and the Km ADH4 gene may be those encoding proteins comprising amino acid sequences exhibiting 80% or higher, preferably 85% or higher, more preferably 90% or higher, further preferably 95% or higher, and most preferably 98% or higher similarity to the amino acid sequences as shown in SEQ ID NOs: 2 and 4, respectively, provided that such genes encode proteins having alcohol dehydrogenase activity. Sequence similarity is determined using a computer equipped with the BLAST (Basic Local Alignment Search Tool) Program, using the default settings.

The Km ADH1 gene and the Km ADH4 gene may be those encoding proteins comprising amino acid sequences derived from the amino acid sequences as shown in SEQ ID NOs: 2 and 4, respectively, by deletion, substitution, addition, or insertion of one or a plurality of (e.g., 2 to 35, preferably 2 to 30, more preferably 2 to 20, and further preferably 2 to 10) amino acids, provided that such genes encode proteins having alcohol dehydrogenase activity.

The Km ADH1 gene and the Km ADH4 gene may be polynucleotides hybridizing under stringent conditions to partial or full-length polynucleotides comprising nucleotide sequences complementary to the nucleotide sequences as shown in SEQ ID NOs: 1 and 3, respectively, provided that such genes encode proteins having alcohol dehydrogenase activity. Under stringent temperature and salt concentration conditions, a pair of polynucleotides having about 90%, preferably 95%, and more preferably 98% identity with each other form specific hybrids.

<Ethanol Production>

With the use of the mutant yeasts described above, ethanol fermentation can be carried out using a sugar such as xylose as a substrate. Since the mutant yeasts according to the present invention described above are excellent in terms of their capacity for xylose metabolism (i.e., the ethanol yield from xylose), such strains are particularly preferable for ethanol fermentation involving the use of a xylose-containing medium. In a xylose-containing medium, a yeast of the genus *Kluyveromyces* can grow, and it at least contains xylose as a sugar component that functions as a substrate for ethanol synthesis. A xylose-containing medium may contain a sugar component other than xylose, such as glucose.

A xylose-containing medium is not particularly limited, and it can be prepared by adding xylose to various types of synthetic media, including SD, YPD, YPAD, YM, and Yeast Nitrogen Base media. Alternatively, a sugar component contained in such known medium may be replaced with xylose, so as to prepare a xylose-containing medium.

Alternatively, a xylose-containing medium may be prepared from lignocellulose-containing biomass such as woody biomass or herbaceous biomass. Specifically, cellulose or hemicellulose contained in lignocellulose-containing biomass may be saccharified, and the resultant may then be used as a xylose-containing medium. Saccharification may be carried out via any conventional means without particular limitation. For example, saccharification may be carried out by a sulfuric acid method involving the use of dilute or concentrated sulfuric acid or by an enzymatic method involving the use of cellulase or hemicellulose. Woody biomass or herbaceous biomass may be subjected to conventional pre-treatment prior to saccharification. Such pre-treatment is not particularly limited, and examples thereof include degradation of lignin with a microorganism, grinding of woody biomass or herbaceous biomass, relaxation of the lignin structure via soaking in an ionic or alkaline solution, hydrothermal treatment via steaming in hot water, and ammonia treatment.

In particular, a mutant yeast prepared from *Kluyveromyces marxianus* is excellent in terms of thermotolerance, and ethanol fermentation can thus be performed at a relatively high temperature, such as 40 degrees C. or higher, preferably 35 degrees C. to 48 degrees C., and more preferably 40 degrees C. to 42 degrees C. In such a temperature range, carbohydrases such as cellulase and hemicellulose exhibit activity. Therefore, such mutant yeast is preferable for the so-called simultaneous saccharification and fermentation process involving the use of a carbohydrase. The simultaneous saccharification and fermentation process comprises saccharification of woody biomass with carbohydrase and ethanol fermentation from xylose carried out in the same reaction system. More specifically, a solution containing woody biomass, carbohydrase, and a mutant yeast is incubated at, for example, 40 degrees C. Thus, saccharification of woody biomass and fermentation of ethanol from xylose or glucose resulting from saccharification proceed, and ethanol can then be produced. In this process, the solution may be subjected to agitation or shaking.

When recovering ethanol produced via fermentation from a carbon source such as xylose contained in a medium, any conventional technique can be employed without particular limitation. After the completion of ethanol fermentation described above, for example, a liquid phase containing ethanol is separated from a solid phase containing a mutant yeast and a solid component via solid-liquid separation. Thereafter, ethanol contained in the liquid phase is separated and purified via distillation, and high-purity ethanol can be thus recovered. The degree of ethanol purification can adequately be adjusted in accordance with the application of ethanol.

EXAMPLES

Hereafter, the present invention is described in greater detail with reference to the examples below, although the technical scope of the present invention is not limited to these examples.

Example 1

In this example, *Kluyveromyces marxianus* was used as a yeast of the genus *Kluyveromyces* to prepare alcohol dehydrogenase gene-deficient strains, and the ethanol yield from xylose was examined.
<Preparation of Strains>
<Preparation of ura3-leu2-Mutant Via Conjugation and Sporulation>

The RAK3605 strain, a ura3-strain of the *Kluyveromyces marxianus* DMKU3-1042 strain (Nonklang, S. et al., Appl. Environ. Microbiol. 74, pp. 7514-7521, 2008), was used as the type strain. An auxotrophic mutant derived from the *K. marxianus* DMKU3-1042 strain was demonstrated to become a diploid at low frequency. While a multiple auxotrophic mutant can be obtained via mutation by ultraviolet radiation, the probability of introduction of a mutation into chromosome DNA is consequently increased. In order to prepare a more stable strain, the strains described below were prepared via conjugation and sporulation for easy production of a multiple auxotrophic mutant from a diploid.

At the outset, the RAK3605 was irradiated with ultraviolet rays to obtain the lys-strain (the RAK3896 strain: ura3-lys2-), the ade-strain (the RAK3919 strain: ura3-ade2-), and the leu-strain (the RAK3966 strain: ura3-leu2-). URA3 of *Saccharomyces cerevisiae* was transformed into the chromosomes of such strains at random to obtain the RAK4088 strain (ura3-leu2-ScURA3), the RAK4152 strain (ura3-ade2-ScURA3), and the RAK4153 strain (ura3-lys2-ScURA3). The RAK4152 strain and the RAK4153 strain were streaked onto YPD medium (1% w/v yeast extract, 2% w/v peptone, 2% glucose, and 2% w/v agar) to be mixed with each other thereon, and the resultants were replicated in MM medium (0.17% w/v yeast nitrogen base w/o amino acids and ammonium sulfate, 0.5% w/v ammonium sulfate, 2% w/v glucose, and 2% w/v agar). The RAK4154 strains grown in MM medium (ura3-/ura3-ade2-/ADE2 and lys2-/LYS2 ScURA3/ScURA3) were inoculated into SPO medium used for *S. cerevisiae* (1% w/v potassium acetate, 0.1% w/v yeast extract, and 0.05% w/v glucose) for sporulation.

The obtained spores were separated and replicated in −A medium (MM+ uracil, tryptophan, histidine HCl, methionine, leucine, lysine HCl), −K medium (MM+ uracil, tryptophan, histidine HCl), methionine, leucine, adenine hemisulfate), −U medium (MM+ tryptophan, histidine HCl, methionine, leucine, lysine HCl, adenine hemisulfate) in order to obtain triple autotrophic strains (i.e., ura-, lys-, ade-). Three strains that could not grow in three media were obtained from the spores of the RAK4154 strain and these strains were designated to be the RAK4155 strains (ura3-, lys2-, ade2-). The RAK4088 strain was conjugated to the RAK4155 strain in the same manner to prepare the RAK4156 strain (ura3-/ura3-lys2-/LYS2 ade2-/ADE2 leu2-/LEU2 ScURA3/ScURA3). The resulting strain was subjected to sporulation to prepare the RAK4174 strain (leu2-ura3-).
<Preparation of Ku70-Deficient Strain>

*K. marxianus* causes non-homologous end-joining repair with high frequency. Accordingly, gene destruction cannot be easily achieved via homologous recombination repair as in the case of *S. cerevisiae* (Nonklang, S. et al., Appl. Environ. Microbiol. 74, pp. 7514-7521, 2008). Accordingly, a strain causing homologous recombination with high frequency was prepared by destroying the KU70 gene necessary for non-homologous end-joining repair. The RAK4736 strain (leu2-ura3-Kmku70Δ::ScLEU2) was prepared from the RAK4174 strain via destruction of KU70 (Abdel-Banat, B. M. et al., Yeast 27, 29-39, 2010).
<Preparation of ADH1-Deficient Strain>

A putative open reading frame of the ADH1 gene of the *K. marxianus* DMKU3-1042 strain was identified with the aid of Genetyx ver.10 (Genetyx Corporation). The ADH1 gene of the *K. marxianus* DMKU3-1042 strain was found to encode a protein comprising 348 amino acids. The pair of primers shown below were designed based on the nucleotide sequence information.

```
KmADH1-167-ASC:                          (SEQ ID NO: 5)
5'-GGGGGCACTTCGAACGCTGAAGTATCTTCATCTGGAGTATACCTTTT

TTTCGCCACTGGAggcgcgcccggg-3'

KmADH1 + 1070c-TDHu:                     (SEQ ID NO: 6)
5'-TACCATATCAAAAGGGTCCTTGCTTATTTGGAAGTGTCAACGACAAT

TCTACCAATGATTtggcagtattgataatgag-3'
```

In the nucleotide sequences of the primers shown above, uppercase letters represent regions homologous to ADH1. ScURA3 was synthesized from the pST106 vector (Ano, A. et al., Biosci. Biotechnol. Biochem., 73, pp. 633-640, 2009) with the use of the above pair of primers and transformed into the RAK4736 strain. As a result, the RAK6148 strain (ura3-leu2-ku70Δ::ScLEU2 adh1Δ::ScURA3) was obtained.
<Preparation of ADH4-Deficient Strain>

A putative open reading frame of the ADH4 gene of the *K. marxianus* DMKU3-1042 strain was identified with the aid of Genetyx ver.10 (Genetyx Corporation). The ADH4 gene of the *K. marxianus* DMKU3-1042 strain was found to encode a protein comprising 379 amino acids. The pair of primers shown below were designed based on the nucleotide sequence information.

```
KmADH4-60-ASC:                           (SEQ ID NO: 7)
5'-CGTACACCCTCAAGCTCATCGCCCGTACACCCACATTATACTATTAA

TAAACCACAAACAggcgcgcccggg-3'

KmADH4 + 1206c:                          (SEQ ID NO: 8)
5'-GAAGGATCATCCAAATGAAAAGAAAGGGACGTTAAGTTAGCATAGCT

TAGTTGGACTGAGtggcagtattgataatgag-3'
```

In the nucleotide sequences of the primers shown above, uppercase letters represent regions homologous to ADH4.

ScURA3 was synthesized from the pST106 vector with the use of the above pair of primers and transformed into the RAK4736 strain. As a result, the RAK6150 strain (ura3-leu2-ku70Δ::ScLEU2 adh4Δ::ScURA3) was prepared.

<Preparation of ADH2-Deficient Strain>

A putative open reading frame of the ADH2 gene of the K. marxianus DMKU3-1042 strain was identified with the aid of Genetyx ver.10 (Genetyx Corporation). The ADH2 gene of the K. marxianus DMKU3-1042 strain was found to encode a protein comprising 348 amino acids, as with the case of the ADH1 gene. The pair of primers shown below were designed based on the nucleotide sequence information.

```
KmADH2-764:                         (SEQ ID NO: 9)
5'-CCCACCCACCCACTGCTACA-3'

KmADH2-1c:                          (SEQ ID NO: 10)
5'-catttctagttgttggttgttgttt-3'
```

The upstream region of the ADH2 open reading frame was synthesized using the pair of primers and the DMKU3-1042 genome of K. marxianus as a template.

Also, the pair of primers shown below were designed based on the nucleotide sequence of the ADH2 gene.

```
KmADH2 + 1045:                      (SEQ ID NO: 11)
5'-GCGGACTAACTAGCCCATTAGT-3'

KmADH2-2141c:                       (SEQ ID NO: 12)
5'-CCCCACGCACAACGTAAACCTT-3'
```

The downstream region of the ADH2 open reading frame was synthesized using the pair of primers and the DMKU3-1042 genome of K. marxianus as a template.

Separately, the ScURA3 gene was synthesized from S. cerevisiae BY4704 (MATa ade2Δ::hisG his3Δ200 leu2Δ0 met15Δ0 trp1Δ63) in accordance with a conventional technique.

The thus-obtained ScURA3 gene was fused to a position between the ADH2 upstream region and the ADH2 downstream region for transformation into the RAK3605 strain. As a result, the RAK6396 strain (ura3-adh2Δ::ScURA3) was obtained.

<Preparation of ADH3-Deficient Strain>

A putative open reading frame of the ADH3 gene of the K. marxianus DMKU3-1042 strain was identified with the aid of Genetyx ver.10 (Genetyx Corporation). The ADH3 gene of the K. marxianus DMKU3-1042 strain was found to encode a protein comprising 375 amino acids. The pair of primers shown below were designed based on the nucleotide sequence thereof.

```
KmADH3-842:                         (SEQ ID NO: 13)
5'-GGCCTGGGTTACCACTGGTCCCCTG-3'

KmADH3-1c:                          (SEQ ID NO: 14)
5'-tgttgcgtgatattttctgtgcctg-3'
```

The upstream region of the ADH3 open reading frame was synthesized using the pair of primers and the DMKU3-1042 genome of K. marxianus as a template.

Also, the pair of primers shown below were designed based on the nucleotide sequence of the ADH3 gene.

```
KmADH3 + 1076:                      (SEQ ID NO: 15)
5'-TGGAACAAGGTAAGATCTTGGG-3'

KmADH3 + 2069c:                     (SEQ ID NO: 16)
5'-TTGCAGGATCCAGAATGGGTCAGTG-3'
```

The downstream region of the ADH3 open reading frame was synthesized using the pair of primers and the DMKU3-1042 genome of K. marxianus as a template.

As with the case of the ADH2-deficient strain, ScURA3 was fused to a position between the ADH3 upstream region and the ADH3 downstream region for transformation into the RAK3605 strain. As a result, the RAK6398 strain (ura3-adh3Δ::ScURA3) was obtained.

<Ethanol Fermentation Test>

The ADH1-deficient strain, the ADH2-deficient strain, the ADH3-deficient strain, and the ADH4-deficient strain prepared in the manner described above were subjected to an ethanol fermentation test using glucose and an ethanol fermentation test using xylose.

<Pre-Culture>

A platinum loopful of the deficient strains described above was introduced into a 50-ml assist tube supplemented with 20 ml of YPX (20 g/l xylose) medium, and shake culture was carried out at 30 degrees C. and 140 rpm for 6 to 8 hours. Subsequently, a 2.5% yeast solution was subjected to shake culture in a 500-ml triangular flask supplemented with 200 ml of YPX (20 g/l xylose) medium at 30 degrees C. and 140 rpm overnight. The cultured yeast strains were centrifuged and washed three times with sterile water to prepare a yeast suspension (OD 600 of 30).

<Main Culture>

Culture was conducted under the conditions shown in Table 1, and sugar consumption, growth of yeast strains, and ethanol production were examined. Culture was conducted with an initial glucose concentration of 50 g/l and with an initial xylose concentration of 20 g/l, respectively.

TABLE 1

| Conditions of experiments | | | | |
| --- | --- | --- | --- | --- |
| Liquid amount | Container | Initial O.D. | Temperature | Number of revolutions |
| 25 ml | 50-ml assist tube | 1 | 30 degrees C. | 140 rpm |

Growth of yeast strains was evaluated by measuring the yeast density using a spectrophotometer (UV-1800, λ=600, Shimadzu Corporation). The amount of sugar and the concentration of ethanol in the medium were measured using the HPLC RI detector (Shimadzu Corporation).

<Results>

Figure 2:
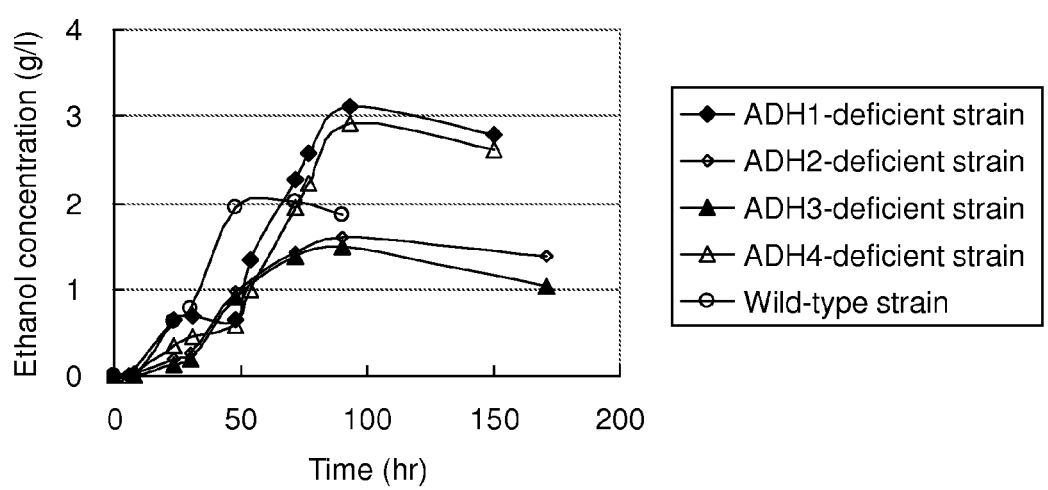
FIG. 2 is a characteristic diagram showing changes in ethanol concentration in a xylose-containing medium when four types of ADF-deficient strains are cultured therein.
Figure 3:
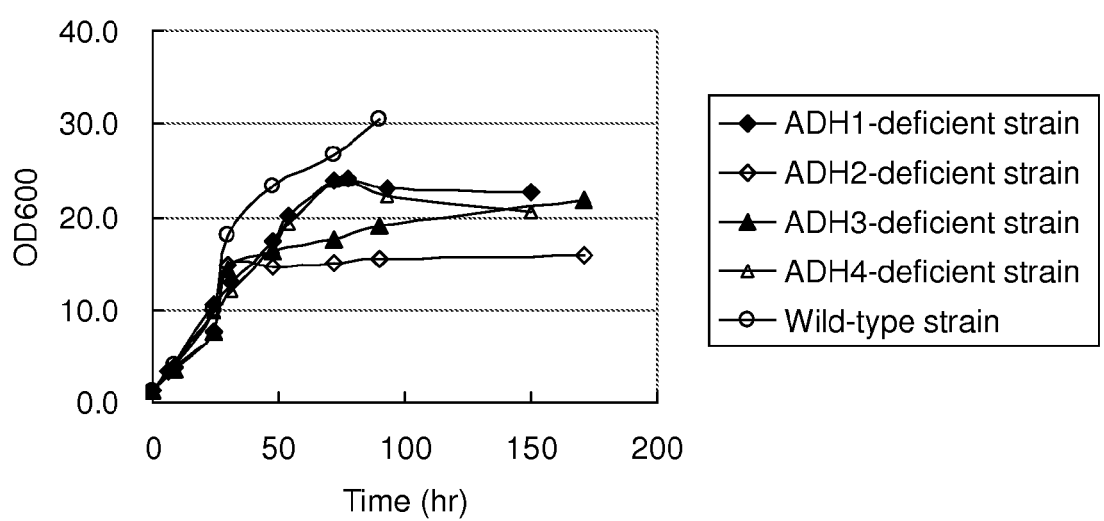
FIG. 3 is a characteristic diagram showing changes in concentration of yeast when four types of ADF-deficient strains are cultured in a xylose-containing medium.

FIG. 1 to FIG. 3 show "changes in xylose concentration in a medium," "changes in ethanol concentration in a medium," "changes in xylitol concentration in a medium," and "changes in concentration of yeasts" from when the deficient strains were cultured in a medium containing xylose as a sugar component. In comparison with a wild-type strain, all the ADH-deficient strains showed lower rates of xylose consumption, as shown in FIG. 1. The significantly lower rate of xylose consumption was observed particularly in the ADH2-deficient strain and the ADH3-deficient strain. As shown in FIG. 2, the ADH1-deficient strain and the ADH4-deficient strain exhibited the ethanol yield from xylose, which was significantly improved over that of a wild-type strain. However, no improvement was observed in the ethanol yield attained with the ADH2-deficient strain or the ADH3-deficient strain. As shown in FIG. 3, the capacity of the ADH1- deficient strain and the ADH4-deficient strain for growth of yeast strains was found to be equivalent to that of a wild-type strain. In comparison with a wild-type strain, however, the capacity of the ADH2-deficient strain and the ADH3-deficient strain for growth of yeast strains was found to be poorer.

Figure 4:
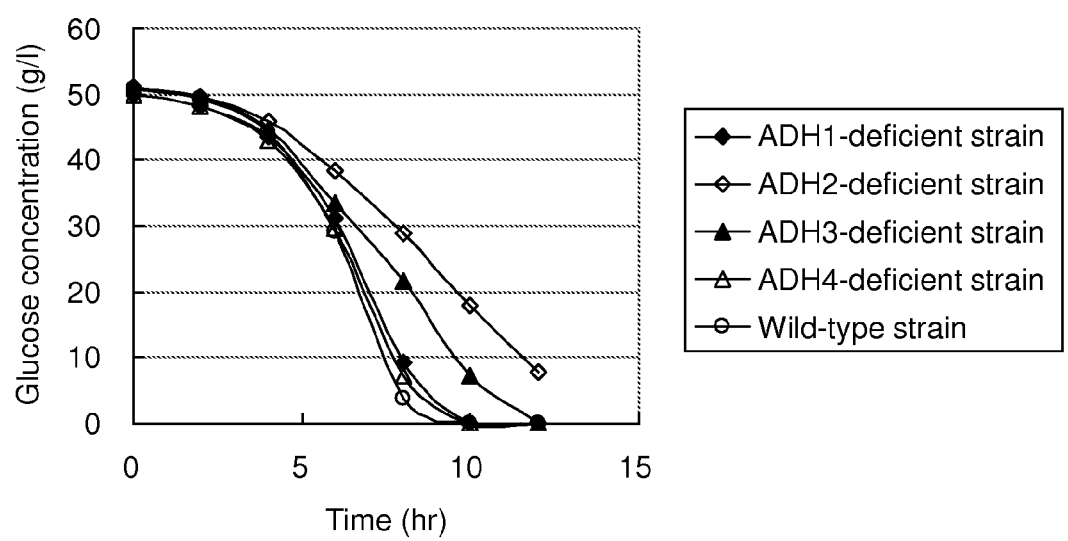
FIG. 4 is a characteristic diagram showing changes in xylitol concentration in a glucose-containing medium when four types of ADF-deficient strains are cultured therein.
Figure 5:
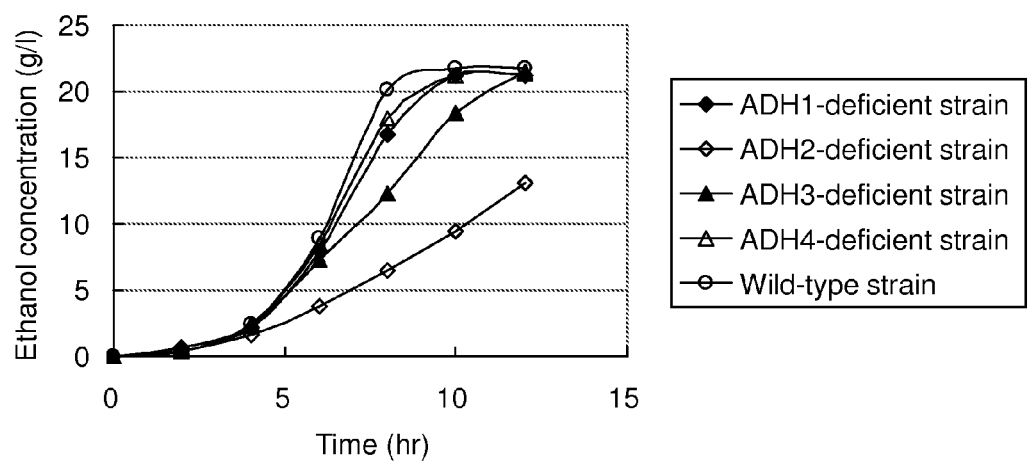
FIG. 5 is a characteristic diagram showing changes in ethanol concentration in a glucose-containing medium when four types of ADF-deficient strains are cultured therein.
Figure 6:
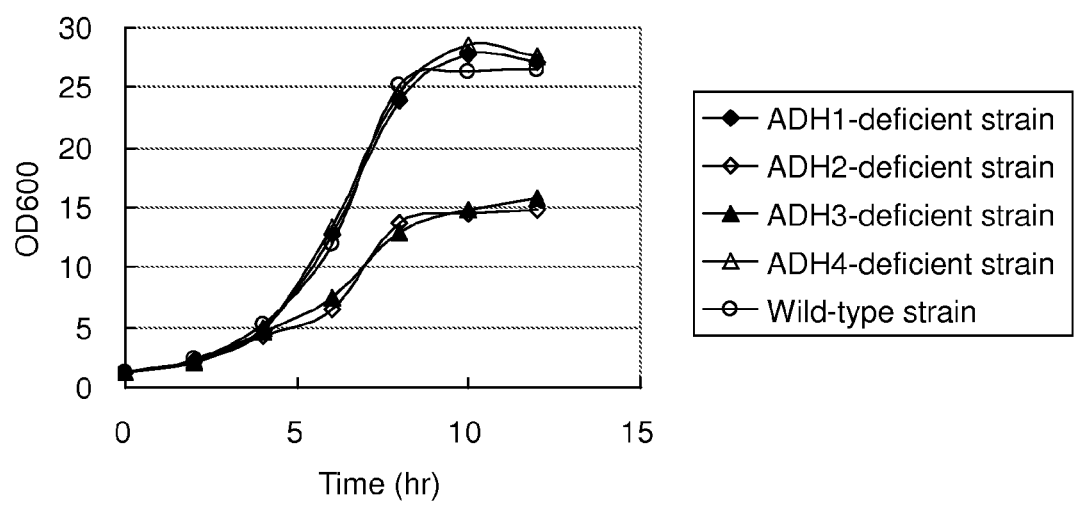
FIG. 6 is a characteristic diagram showing changes in concentration of yeast when four types of ADF-deficient strains are cultured in a glucose-containing medium.

FIG. 4 to FIG. 6 show "changes in glucose concentration in a medium," "changes in ethanol concentration in a medium," "changes in glycerol concentration in a medium," and "changes in concentration of yeasts" when the deficient strains were cultured in a medium containing glucose as a sugar component. As shown in FIG. 4 to FIG. 6, the ethanol yield attained by culturing the deficient strains using glucose was equivalent to or lower than that attained with a wild-type strain. That is, destruction of the ADH genes was found to have no influence on glucose intake, ethanol fermentation from glucose, ethanol productivity in ethanol fermentation utilizing glucose, or other activity. In the case of yeasts of the genus *Kluyveromyces*, however, attenuation of the ADH1 gene and the ADH4 gene of was found to specifically improve the ethanol yield from xylose.

FIGS. 7 to 14 show the results of examination of homology at amino acid levels between ADH1 or ADH2 derived from *S. cerevisiae* and each of ADH1 to ADH4 derived from *K. marxianus* for reference purposes. FIG. 7 shows the alignment of ADH1 derived from *S. cerevisiae* with ADH1 derived from *K. marxianus*. FIG. 8 shows the alignment of ADH1 derived from *S. cerevisiae* with ADH2 derived from *K. marxianus*. FIG. 9 shows the alignment of ADH1 derived from *S. cerevisiae* with ADH3 derived from *K. marxianus*. FIG. 10 shows the alignment of ADH1 derived from *S. cerevisiae* with ADH4 derived from *K. marxianus*. FIG. 11 shows the alignment of ADH2 derived from *S. cerevisiae* with ADH1 derived from *K. marxianus*. FIG. 12 shows the alignment of ADH2 derived from *S. cerevisiae* with ADH2 derived from *K. marxianus*. FIG. 13 shows the alignment of ADH2 derived from *S. cerevisiae* with ADH3 derived from *K. marxianus*. FIG. 14 shows the alignment of ADH2 derived from *S. cerevisiae* with ADH4 derived from *K. marxianus*.

As shown in FIG. 7, the identity and the similarity between ADH1 derived from *S. cerevisiae* and ADH1 derived from *K. marxianus* were 79% and 97%, respectively. As shown in FIG. 8, the identity and the similarity between ADH1 derived from *S. cerevisiae* and ADH2 derived from *K. marxianus* were 86% and 96%, respectively. As shown in FIG. 9, the identity and the similarity between ADH1 derived from *S. cerevisiae* and ADH3 derived from *K. marxianus* were 79% and 96%, respectively. As shown in FIG. 10, the identity and the similarity between ADH1 derived from *S. cerevisiae* and ADH4 derived from *K. marxianus* were 80% and 94%, respectively. As shown in FIG. 11, the identity and the similarity between ADH2 derived from *S. cerevisiae* and ADH1 derived from *K. marxianus* were 79% and 97%, respectively. As shown in FIG. 12, the identity and the similarity between ADH2 derived from *S. cerevisiae* and ADH2 derived from *K. marxianus* were 84% and 96%, respectively. As shown in FIG. 13, the identity and the similarity between ADH2 derived from *S. cerevisiae* and ADH3 derived from *K. marxianus* were 78% and 96%, respectively. As shown in FIG. 14, the identity and the similarity between ADH2 derived from *S. cerevisiae* and ADH4 derived from *K. marxianus* were 80% and 95%, respectively.

FIG. 15 shows the alignment of ADH1 derived from *S. cerevisiae* with ADH2 derived from *S. cerevisiae*. As shown in FIG. 15, the identity and the similarity between ADH1 derived from *S. cerevisiae* and ADH2 derived from *S. cerevisiae* were 93% and 99%, respectively.

As shown in FIGS. 7 to 14, the identity and the similarity between each of ADH1 to ADH4 derived from *K. marxianus* and ADH1 or ADH2 derived from *S. cerevisiae* are very high, and it is difficult to deduce the functions of ADH1 to ADH4 derived from *K. marxianus* from comparison with ADH1 and ADH2 derived from *S. cerevisiae*. Therefore, the outcome to the effect that the ethanol yield from xylose can be specifically improved by attenuation of the ADH1 or ADH4 gene of a yeast of the genus *Kluyveromyces* can be astonishing.

All publications, patents, and patent applications cited herein are incorporated herein by reference in their entirety.

The invention claimed is:

1. A mutant of *Kluyveromyces marxianus* obtained by attenuation of an ADH1 gene and/or an ADH4 gene, wherein the ADH1 gene encodes a protein selected from the group consisting of (a) and (b), and wherein the ADH4 gene encodes a protein selected from the group consisting of (c) and (d):
   (a) a protein comprising the amino acid sequence of SEQ ID NO: 2; and
   (b) a protein comprising an amino acid sequence having 90% or higher similarity to the amino acid sequence of SEQ ID NO: 2 and having alcohol dehydrogenase activity,
   (c) a protein comprising the amino acid sequence of SEQ ID NO: 4; and
   (d) a protein comprising an amino acid sequence having 90% or higher similarity to the amino acid sequence of SEQ ID NO: 4 and having alcohol dehydrogenase activity.

2. A method for producing ethanol, comprising:
   (1) culturing a mutant of *Kluyveromyces marxianus* in a xylose-containing medium, said mutant having been obtained by attenuation of an ADH1 gene and/or an ADH4 gene, wherein the ADH1 gene encodes a protein selected from the group consisting of (a) and (b), and wherein the ADH4 gene encodes a protein selected from the group consisting of (c) and (d):
   (a) a protein comprising the amino acid sequence of SEQ ID NO: 2; and
   (b) a protein comprising an amino acid sequence having 90% or higher similarity to the amino acid sequence of SEQ ID NO: 2 and having alcohol dehydrogenase activity,
   (c) a protein comprising the amino acid sequence of SEQ ID NO: 4; and
   (d) a protein comprising an amino acid sequence having 90% or higher similarity to the amino acid sequence of SEQ ID NO: 4 and having alcohol dehydrogenase activity, and
   (2) recovering ethanol from the medium.

3. The method according to claim 2, wherein said culturing is carried out in a reaction system containing the mutant of *Kluyveromyces marxianus*, lignocellulose-containing biomass, and a carbohydrase.

* * * * *

SEQUENCE LISTING

```
<160> NUMBER OF SEQ ID NOS: 16

<210> SEQ ID NO 1
<211> LENGTH: 1047
<212> TYPE: DNA
<213> ORGANISM: Kluyveromyces marxianus
<220> FEATURE:
<221> NAME/KEY: CDS
<222> LOCATION: (1)..(1047)

<400> SEQUENCE: 1 atg gct att cca gaa act caa aag ggt gtt atc ttc tac gaa aac ggt      48
Met Ala Ile Pro Glu Thr Gln Lys Gly Val Ile Phe Tyr Glu Asn Gly
1               5                   10                  15 ggt gag ttg caa tac aag gac att cca gtt cca aag cca aag cca aac      96
Gly Glu Leu Gln Tyr Lys Asp Ile Pro Val Pro Lys Pro Lys Pro Asn
            20                  25                  30 gaa ctt ttg atc aac gtt aag tac tct ggt gtg tgt cac acc gat ttg     144
Glu Leu Leu Ile Asn Val Lys Tyr Ser Gly Val Cys His Thr Asp Leu
        35                  40                  45 cac gca tgg caa ggt gac tgg cca ttg gac acc aag ttg cca ttg gtg     192
His Ala Trp Gln Gly Asp Trp Pro Leu Asp Thr Lys Leu Pro Leu Val
    50                  55                  60 ggt ggt cac gaa ggt gct ggt att gtt gtt gcc atg ggt gag aac gtt     240
```

| | | | |
|---|---|---|---|
| Gly Gly His Glu Gly Ala Gly Ile Val Val Ala Met Gly Glu Asn Val<br>65                          70                         75                    80 | | | |

```
act ggc tgg gaa atc ggt gac tat gct ggt atc aag tgg ttg aac ggt    288
Thr Gly Trp Glu Ile Gly Asp Tyr Ala Gly Ile Lys Trp Leu Asn Gly
             85                  90                  95 tcc tgt atg tct tgt gag gag tgt gag ttg tcg aac gaa cca aac tgt    336
Ser Cys Met Ser Cys Glu Glu Cys Glu Leu Ser Asn Glu Pro Asn Cys
        100                 105                 110 cca aag gcc gac ttg tct ggt tac aca cac gac ggt tct ttc caa caa    384
Pro Lys Ala Asp Leu Ser Gly Tyr Thr His Asp Gly Ser Phe Gln Gln
    115                 120                 125 tac gct acc gct gac gct gtc cag gct gcc aga att cca aag aac gtc    432
Tyr Ala Thr Ala Asp Ala Val Gln Ala Ala Arg Ile Pro Lys Asn Val
130                 135                 140 gac ttg gcc gag gtt gcc cca atc ttg tgt gcc ggt gtt acc gtg tac    480
Asp Leu Ala Glu Val Ala Pro Ile Leu Cys Ala Gly Val Thr Val Tyr
145                 150                 155                 160 aag gct ttg aag tct gct cac atc aag gct ggt gac tgg gtc gcc atc    528
Lys Ala Leu Lys Ser Ala His Ile Lys Ala Gly Asp Trp Val Ala Ile
                165                 170                 175 tct ggt gca tgt ggt ggt cta ggt tcc ttg gcc atc caa tac gcc aag    576
Ser Gly Ala Cys Gly Gly Leu Gly Ser Leu Ala Ile Gln Tyr Ala Lys
            180                 185                 190 gct atg ggt tac aga gtg cta ggt atc gat gct ggt gac gaa aag gcc    624
Ala Met Gly Tyr Arg Val Leu Gly Ile Asp Ala Gly Asp Glu Lys Ala
        195                 200                 205 aaa ttg ttc aag gaa ttg ggc ggt gaa tac ttt atc gac ttt acc aag    672
Lys Leu Phe Lys Glu Leu Gly Gly Glu Tyr Phe Ile Asp Phe Thr Lys
    210                 215                 220 acc aag gat atg gta gca gaa gtc att gag gcc acc aac ggt ggt gcc    720
Thr Lys Asp Met Val Ala Glu Val Ile Glu Ala Thr Asn Gly Gly Ala
225                 230                 235                 240 cac gcc gtc att aac gtg tct gtg tcc gaa gcc gcc atc tct acc tct    768
His Ala Val Ile Asn Val Ser Val Ser Glu Ala Ala Ile Ser Thr Ser
                245                 250                 255 gtc ttg tac acc aga tca aac ggt acc gtc gtc ttg gtc ggt ttg cca    816
Val Leu Tyr Thr Arg Ser Asn Gly Thr Val Val Leu Val Gly Leu Pro
            260                 265                 270 aga gac gct caa tgt aag tct gat gtc ttc aac caa gtc gtc aag tcc    864
Arg Asp Ala Gln Cys Lys Ser Asp Val Phe Asn Gln Val Val Lys Ser
        275                 280                 285 atc tcc att gtt ggt tct tac gtt ggt aac aga gca gac acc aga gaa    912
Ile Ser Ile Val Gly Ser Tyr Val Gly Asn Arg Ala Asp Thr Arg Glu
    290                 295                 300 gcc cta gac ttc ttc tcc aga ggt ttg gtc aag gcc cca att aag att    960
Ala Leu Asp Phe Phe Ser Arg Gly Leu Val Lys Ala Pro Ile Lys Ile
305                 310                 315                 320 ctc ggc ttg tcc gaa ttg gca acc gtt tac gac aag atg tcc aag ggc   1008
Leu Gly Leu Ser Glu Leu Ala Thr Val Tyr Asp Lys Met Ser Lys Gly
                325                 330                 335 caa atc att ggt aga att gtc gtt gac act tcc aaa taa               1047
Gln Ile Ile Gly Arg Ile Val Val Asp Thr Ser Lys
            340                 345
```

<210> SEQ ID NO 2
<211> LENGTH: 348
<212> TYPE: PRT
<213> ORGANISM: Kluyveromyces marxianus

<400> SEQUENCE: 2

```
Met Ala Ile Pro Glu Thr Gln Lys Gly Val Ile Phe Tyr Glu Asn Gly
 1               5                  10                  15

Gly Glu Leu Gln Tyr Lys Asp Ile Pro Val Pro Lys Pro Lys Pro Asn
            20                  25                  30

Glu Leu Leu Ile Asn Val Lys Tyr Ser Gly Val Cys His Thr Asp Leu
            35                  40                  45

His Ala Trp Gln Gly Asp Trp Pro Leu Asp Thr Lys Leu Pro Leu Val
    50                  55                  60

Gly Gly His Glu Gly Ala Gly Ile Val Val Ala Met Gly Glu Asn Val
65                  70                  75                  80

Thr Gly Trp Glu Ile Gly Asp Tyr Ala Gly Ile Lys Trp Leu Asn Gly
                85                  90                  95

Ser Cys Met Ser Cys Glu Glu Cys Leu Ser Asn Glu Pro Asn Cys
                100                 105                 110

Pro Lys Ala Asp Leu Ser Gly Tyr Thr His Asp Gly Ser Phe Gln Gln
            115                 120                 125

Tyr Ala Thr Ala Asp Ala Val Gln Ala Ala Arg Ile Pro Lys Asn Val
    130                 135                 140

Asp Leu Ala Glu Val Ala Pro Ile Leu Cys Ala Gly Val Thr Val Tyr
145                 150                 155                 160

Lys Ala Leu Lys Ser Ala His Ile Lys Ala Gly Asp Trp Val Ala Ile
                165                 170                 175

Ser Gly Ala Cys Gly Gly Leu Gly Ser Leu Ala Ile Gln Tyr Ala Lys
                180                 185                 190

Ala Met Gly Tyr Arg Val Leu Gly Ile Asp Ala Gly Asp Glu Lys Ala
            195                 200                 205

Lys Leu Phe Lys Glu Leu Gly Gly Glu Tyr Phe Ile Asp Phe Thr Lys
    210                 215                 220

Thr Lys Asp Met Val Ala Glu Val Ile Glu Ala Thr Asn Gly Gly Ala
225                 230                 235                 240

His Ala Val Ile Asn Val Ser Val Ser Glu Ala Ala Ile Ser Thr Ser
                245                 250                 255

Val Leu Tyr Thr Arg Ser Asn Gly Thr Val Val Leu Val Gly Leu Pro
            260                 265                 270

Arg Asp Ala Gln Cys Lys Ser Asp Val Phe Asn Gln Val Val Lys Ser
    275                 280                 285

Ile Ser Ile Val Gly Ser Tyr Val Gly Asn Arg Ala Asp Thr Arg Glu
    290                 295                 300

Ala Leu Asp Phe Phe Ser Arg Gly Leu Val Lys Ala Pro Ile Lys Ile
305                 310                 315                 320

Leu Gly Leu Ser Glu Leu Ala Thr Val Tyr Asp Lys Met Ser Lys Gly
                325                 330                 335

Gln Ile Ile Gly Arg Ile Val Val Asp Thr Ser Lys
            340                 345

<210> SEQ ID NO 3
<211> LENGTH: 1140
<212> TYPE: DNA
<213> ORGANISM: Kluyveromyces marxianus
<220> FEATURE:
<221> NAME/KEY: CDS
<222> LOCATION: (1)..(1140)

<400> SEQUENCE: 3 atg ttc aga cta gca cgc gct cag acc agc att acc acc act agc aag    48
Met Phe Arg Leu Ala Arg Ala Gln Thr Ser Ile Thr Thr Thr Ser Lys
```

```
 1             5                     10                    15
gct cta ggt ggc tcc aga aga cta ttc gtc aga cta aac tcc tct ttc     96
Ala Leu Gly Gly Ser Arg Arg Leu Phe Val Arg Leu Asn Ser Ser Phe
         20                  25                  30 gcc atc cca gaa tcc caa aag ggt gtg att ttc tac gaa aac ggc ggt    144
Ala Ile Pro Glu Ser Gln Lys Gly Val Ile Phe Tyr Glu Asn Gly Gly
             35                  40                  45 aag ttg gaa tac aag gac ctt cca gtt cca aag cca aag cca aat gaa    192
Lys Leu Glu Tyr Lys Asp Leu Pro Val Pro Lys Pro Lys Pro Asn Glu
50                  55                  60 atc ttg atc aac gtc aag tac tcc ggt gtg tgt cac act gat ttg cac    240
Ile Leu Ile Asn Val Lys Tyr Ser Gly Val Cys His Thr Asp Leu His
65                  70                  75                  80 gcc tgg aag ggt gac tgg cca ttg cca gtt aag ttg cct ttg gtc ggt    288
Ala Trp Lys Gly Asp Trp Pro Leu Pro Val Lys Leu Pro Leu Val Gly
                 85                  90                  95 ggt cac gaa ggt gcc ggt gtc gtc gtt gcc aag ggt gaa aac gtt acc    336
Gly His Glu Gly Ala Gly Val Val Val Ala Lys Gly Glu Asn Val Thr
             100                 105                 110 aac ttc gag atc ggt gac tac gca ggt atc aag tgg ttg aac ggt tct    384
Asn Phe Glu Ile Gly Asp Tyr Ala Gly Ile Lys Trp Leu Asn Gly Ser
         115                 120                 125 tgt atg tct tgt gaa ctc tgt gaa caa ggt tac gaa tcc aac tgt ttg    432
Cys Met Ser Cys Glu Leu Cys Glu Gln Gly Tyr Glu Ser Asn Cys Leu
     130                 135                 140 caa gct gac ttg tct ggt tac acc cac gac ggt tcc ttc caa caa tat    480
Gln Ala Asp Leu Ser Gly Tyr Thr His Asp Gly Ser Phe Gln Gln Tyr
145                 150                 155                 160 gcc act gct gac gct gtt caa gct gcc caa att cca aag ggt acc gat    528
Ala Thr Ala Asp Ala Val Gln Ala Ala Gln Ile Pro Lys Gly Thr Asp
                 165                 170                 175 ttg gct gaa atc gcc cca atc ttg tgt gcc ggt gtc acc gtc tac aag    576
Leu Ala Glu Ile Ala Pro Ile Leu Cys Ala Gly Val Thr Val Tyr Lys
             180                 185                 190 gct cta aag acc gct gac ttg caa cca ggt caa tgg atc gct atc tcc    624
Ala Leu Lys Thr Ala Asp Leu Gln Pro Gly Gln Trp Ile Ala Ile Ser
         195                 200                 205 ggt gct gcc ggt ggt ctt ggt tcc cta gcc gtg caa tac gcc aag gca    672
Gly Ala Ala Gly Gly Leu Gly Ser Leu Ala Val Gln Tyr Ala Lys Ala
     210                 215                 220 atg ggt cta aga gtt cta ggt atc gac ggt ggt cca ggt aag gaa gaa    720
Met Gly Leu Arg Val Leu Gly Ile Asp Gly Gly Pro Gly Lys Glu Glu
225                 230                 235                 240 ttg ttc aag agc ttg ggt ggt gaa gtc ttc att gac ttc aca aag tcc    768
Leu Phe Lys Ser Leu Gly Gly Glu Val Phe Ile Asp Phe Thr Lys Ser
                 245                 250                 255 aag gac atg gtc gca gac atc cag gaa gcc acc aac ggt ggt cct cac    816
Lys Asp Met Val Ala Asp Ile Gln Glu Ala Thr Asn Gly Gly Pro His
             260                 265                 270 ggt gtg atc aac gtc tcc gtc tcc gag gcc gct atc tcc atg tcc acc    864
Gly Val Ile Asn Val Ser Val Ser Glu Ala Ala Ile Ser Met Ser Thr
         275                 280                 285 gag tac gtc aga cca acc ggt gtg gtc gtt cta gtc ggt ttg cca gcc    912
Glu Tyr Val Arg Pro Thr Gly Val Val Val Leu Val Gly Leu Pro Ala
     290                 295                 300 cac gct tac gtc aag tcc gaa gtc ttc tcc cac gtc gtc aag tct atc    960
His Ala Tyr Val Lys Ser Glu Val Phe Ser His Val Val Lys Ser Ile
305                 310                 315                 320 tct att aag ggt tct tac gtc ggt aac aga gca gac acc aga gaa gct   1008
```

```
Ser Ile Lys Gly Ser Tyr Val Gly Asn Arg Ala Asp Thr Arg Glu Ala
            325                 330                 335 att gac ttc ttc acc aga ggt ttg gtc aag tct cca atc aag gtt gtt      1056
Ile Asp Phe Phe Thr Arg Gly Leu Val Lys Ser Pro Ile Lys Val Val
            340                 345                 350 ggt ttg tct gaa ttg cca aag gtt tat gaa ttg atg gaa gct ggt aag      1104
Gly Leu Ser Glu Leu Pro Lys Val Tyr Glu Leu Met Glu Ala Gly Lys
            355                 360                 365 atc ttg ggt aga tac gtc gtt gac act tcc aaa taa                      1140
Ile Leu Gly Arg Tyr Val Val Asp Thr Ser Lys
            370                 375

<210> SEQ ID NO 4
<211> LENGTH: 379
<212> TYPE: PRT
<213> ORGANISM: Kluyveromyces marxianus

<400> SEQUENCE: 4

Met Phe Arg Leu Ala Arg Ala Gln Thr Ser Ile Thr Thr Thr Ser Lys
1               5                   10                  15

Ala Leu Gly Gly Ser Arg Arg Leu Phe Val Arg Leu Asn Ser Ser Phe
            20                  25                  30

Ala Ile Pro Glu Ser Gln Lys Gly Val Ile Phe Tyr Glu Asn Gly Gly
        35                  40                  45

Lys Leu Glu Tyr Lys Asp Leu Pro Val Pro Lys Pro Lys Pro Asn Glu
    50                  55                  60

Ile Leu Ile Asn Val Lys Tyr Ser Gly Val Cys His Thr Asp Leu His
65                  70                  75                  80

Ala Trp Lys Gly Asp Trp Pro Leu Pro Val Lys Leu Pro Leu Val Gly
                85                  90                  95

Gly His Glu Gly Ala Gly Val Val Val Ala Lys Gly Glu Asn Val Thr
            100                 105                 110

Asn Phe Glu Ile Gly Asp Tyr Ala Gly Ile Lys Trp Leu Asn Gly Ser
        115                 120                 125

Cys Met Ser Cys Glu Leu Cys Glu Gln Gly Tyr Glu Ser Asn Cys Leu
    130                 135                 140

Gln Ala Asp Leu Ser Gly Tyr Thr His Asp Gly Ser Phe Gln Gln Tyr
145                 150                 155                 160

Ala Thr Ala Asp Ala Val Gln Ala Ala Gln Ile Pro Lys Gly Thr Asp
                165                 170                 175

Leu Ala Glu Ile Ala Pro Ile Leu Cys Ala Gly Val Thr Val Tyr Lys
            180                 185                 190

Ala Leu Lys Thr Ala Asp Leu Gln Pro Gly Gln Trp Ile Ala Ile Ser
        195                 200                 205

Gly Ala Ala Gly Gly Leu Gly Ser Leu Ala Val Gln Tyr Ala Lys Ala
    210                 215                 220

Met Gly Leu Arg Val Leu Gly Ile Asp Gly Gly Pro Gly Lys Glu Glu
225                 230                 235                 240

Leu Phe Lys Ser Leu Gly Gly Glu Val Phe Ile Asp Phe Thr Lys Ser
                245                 250                 255

Lys Asp Met Val Ala Asp Ile Gln Glu Ala Thr Asn Gly Gly Pro His
            260                 265                 270

Gly Val Ile Asn Val Ser Val Ser Glu Ala Ala Ile Ser Met Ser Thr
        275                 280                 285

Glu Tyr Val Arg Pro Thr Gly Val Val Leu Val Gly Leu Pro Ala
    290                 295                 300
```

```
His Ala Tyr Val Lys Ser Glu Val Phe Ser His Val Val Lys Ser Ile
305                 310                 315                 320

Ser Ile Lys Gly Ser Tyr Val Gly Asn Arg Ala Asp Thr Arg Glu Ala
            325                 330                 335

Ile Asp Phe Phe Thr Arg Gly Leu Val Lys Ser Pro Ile Lys Val Val
        340                 345                 350

Gly Leu Ser Glu Leu Pro Lys Val Tyr Glu Leu Met Glu Ala Gly Lys
        355                 360                 365

Ile Leu Gly Arg Tyr Val Val Asp Thr Ser Lys
        370                 375
```

<210> SEQ ID NO 5
<211> LENGTH: 72
<212> TYPE: DNA
<213> ORGANISM: Artificial
<220> FEATURE:
<223> OTHER INFORMATION: Synthetic DNA

<400> SEQUENCE: 5

```
gggggcactt cgaacgctga agtatcttca tctggagtat acctttttt cgccactgga      60 ggcgcgcccg gg                                                         72
```

<210> SEQ ID NO 6
<211> LENGTH: 79
<212> TYPE: DNA
<213> ORGANISM: Artificial
<220> FEATURE:
<223> OTHER INFORMATION: Synthetic DNA

<400> SEQUENCE: 6

```
taccatatca aagggtcct tgcttatttg gaagtgtcaa cgacaattct accaatgatt      60
tggcagtatt gataatgag                                                  79
```

<210> SEQ ID NO 7
<211> LENGTH: 72
<212> TYPE: DNA
<213> ORGANISM: Artificial
<220> FEATURE:
<223> OTHER INFORMATION: Synthetic DNA

<400> SEQUENCE: 7

```
cgtacaccct caagctcatc gcccgtacac ccacattata ctattaataa accacaaaca     60
ggcgcgcccg gg                                                         72
```

<210> SEQ ID NO 8
<211> LENGTH: 79
<212> TYPE: DNA
<213> ORGANISM: Artificial
<220> FEATURE:
<223> OTHER INFORMATION: Synthetic DNA

<400> SEQUENCE: 8

```
gaaggatcat ccaaatgaaa agaaagggac gttaagttag catagcttag ttggactgag     60
tggcagtatt gataatgag                                                  79
```

<210> SEQ ID NO 9
<211> LENGTH: 20
<212> TYPE: DNA
<213> ORGANISM: Artificial
<220> FEATURE:
<223> OTHER INFORMATION: Synthetic DNA

<400> SEQUENCE: 9
cccacccacc cactgctaca                                           20

<210> SEQ ID NO 10
<211> LENGTH: 25
<212> TYPE: DNA
<213> ORGANISM: Artificial
<220> FEATURE:
<223> OTHER INFORMATION: Synthetic DNA

<400> SEQUENCE: 10
catttctagt tgttggttgt tgttt                                     25

<210> SEQ ID NO 11
<211> LENGTH: 22
<212> TYPE: DNA
<213> ORGANISM: Artificial
<220> FEATURE:
<223> OTHER INFORMATION: Synthetic DNA

<400> SEQUENCE: 11
gcggactaac tagcccatta gt                                        22

<210> SEQ ID NO 12
<211> LENGTH: 22
<212> TYPE: DNA
<213> ORGANISM: Artificial
<220> FEATURE:
<223> OTHER INFORMATION: Synthetic DNA

<400> SEQUENCE: 12
ccccacgcac aacgtaaacc tt                                        22

<210> SEQ ID NO 13
<211> LENGTH: 25
<212> TYPE: DNA
<213> ORGANISM: Artificial
<220> FEATURE:
<223> OTHER INFORMATION: Synthetic DNA

<400> SEQUENCE: 13
ggcctgggtt accactggtc ccctg                                     25

<210> SEQ ID NO 14
<211> LENGTH: 25
<212> TYPE: DNA
<213> ORGANISM: Artificial
<220> FEATURE:
<223> OTHER INFORMATION: Synthetic DNA

<400> SEQUENCE: 14
tgttgcgtga tattttctgt gcctg                                     25

<210> SEQ ID NO 15
<211> LENGTH: 22
<212> TYPE: DNA
<213> ORGANISM: Artificial
<220> FEATURE:
<223> OTHER INFORMATION: Synthetic DNA

<400> SEQUENCE: 15
tggaacaagg taagatcttg gg                                        22

<210> SEQ ID NO 16

```
<211> LENGTH: 25
<212> TYPE: DNA
<213> ORGANISM: Artificial
<220> FEATURE:
<223> OTHER INFORMATION: Synthetic DNA

<400> SEQUENCE: 16
ttgcaggatc cagaatgggt cagtg                                          25
```